(12) United States Patent
Shi

(10) Patent No.: US 7,998,161 B2
(45) Date of Patent: Aug. 16, 2011

(54) DISPOSABLE INCISION SAFETY LANCET

(76) Inventor: Guoping Shi, Suzhou (CN)

( * ) Notice: Subject to any disclaimer, the term of this patent is extended or adjusted under 35 U.S.C. 154(b) by 420 days.

(21) Appl. No.: 12/289,202

(22) Filed: Oct. 22, 2008

(65) Prior Publication Data

US 2010/0010529 A1   Jan. 14, 2010

(30) Foreign Application Priority Data

Jul. 9, 2008   (CN) .......................... 2008 1 0023025

(51) Int. Cl.
*A61B 5/151* (2006.01)
(52) U.S. Cl. ....................................................... 606/182
(58) Field of Classification Search .................. 606/117, 606/181–189; 604/131, 134; 600/573, 583
See application file for complete search history.

(56) References Cited

U.S. PATENT DOCUMENTS

| | | | | |
|---|---|---|---|---|
| 4,628,929 A | * | 12/1986 | Intengan et al. | 606/182 |
| 5,314,441 A | * | 5/1994 | Cusack et al. | 606/182 |
| 5,571,132 A | * | 11/1996 | Mawhirt et al. | 606/182 |
| 5,645,555 A | * | 7/1997 | Davis et al. | 606/182 |
| 5,772,677 A | * | 6/1998 | Mawhirt et al. | 606/181 |
| 5,797,940 A | * | 8/1998 | Mawhirt et al. | 606/167 |
| 6,221,089 B1 | * | 4/2001 | Mawhirt | 606/181 |
| 7,704,265 B2 | * | 4/2010 | Schraga | 606/182 |

* cited by examiner

*Primary Examiner* — Anhtuan T Nguyen
*Assistant Examiner* — Rachel S Papeika
(74) *Attorney, Agent, or Firm* — Oliff & Berridge, PLC

(57) ABSTRACT

A disposable incision safety lancet is provided, including a casing (2) and a trigger. It is characterized in that the casing (2) is provided inside with an incision blood-taking mechanism composed of a cam (3), a main swing arm (4), a secondary swing arm (5), a blade (1) and a spring (8). The present invention combines the two arc-shaped tracks obtained from the two swing mechanisms, the main swing arm and the secondary swing arm, via the cam and a toggle pin provided on the cam effectively and interlockingly, thus making the point of the blade incise along a V-formed path composed of two arcs of different shape connected with each other. Compared with the prior art single-swing-arm structure of the incision blood-taking mechanism, such a double-swing-arm structure can move with higher accuracy and controllability. An incision of different blood-taking depth and blood-taking width can be designed by means of changing the difference of change of the radius of curvature of the flange of cam (3) as well as changing the swing radius of the main swing arm (4) and the secondary swing arm (5), which is especially suitable for taking blood from infants' heel.

5 Claims, 5 Drawing Sheets

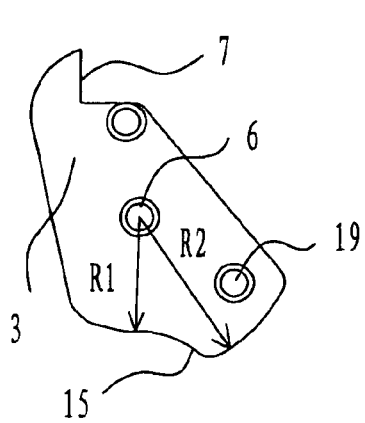
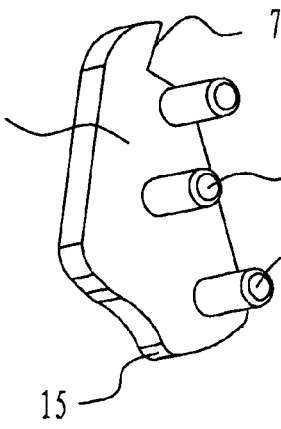
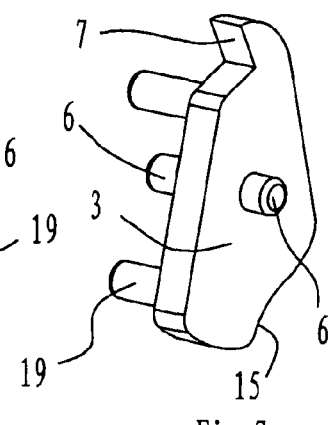
Fig. 5　　　　　Fig. 6　　　　　Fig. 7
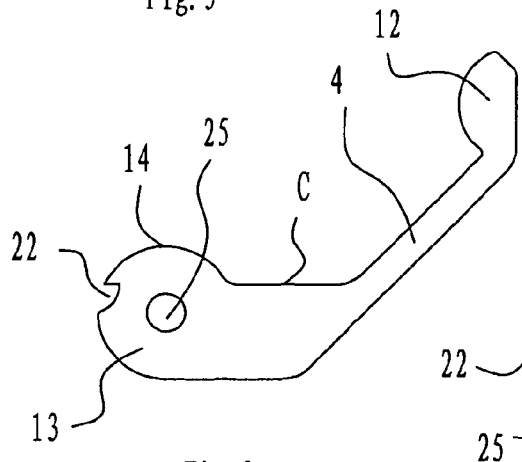
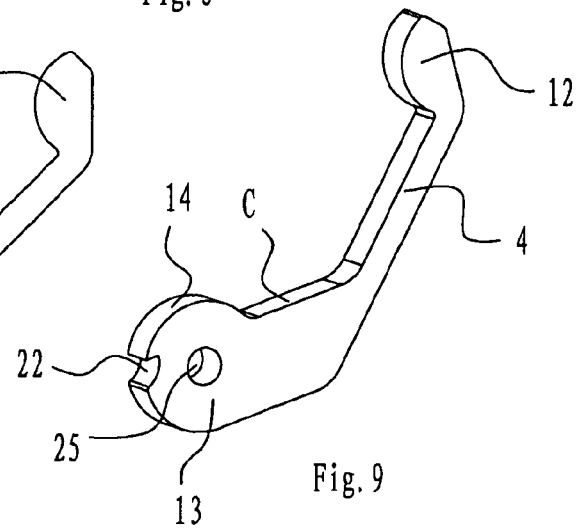
Fig. 8　　　　　　　　Fig. 9
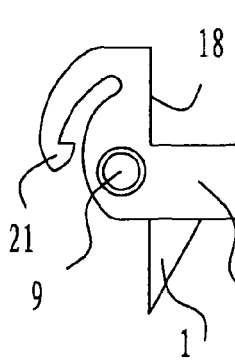
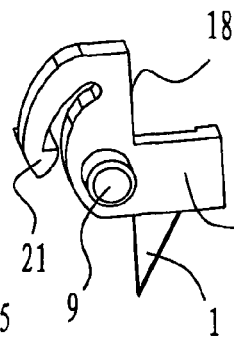
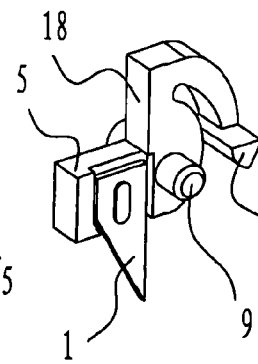
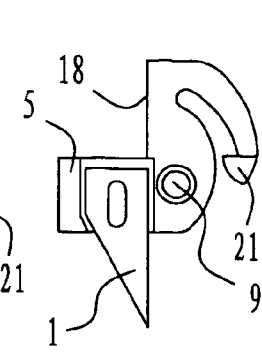
Fig. 10　　Fig. 11　　Fig. 12　　Fig. 13

DISPOSABLE INCISION SAFETY LANCET

FIELD OF THE INVENTION

Belonging to the field of medical apparatus and instruments, the present invention relates particularly to a medical lancet, and more particularly to a disposable incision safety lancet. Such a lancet acts on the blood-taking site of the human body by means of incision of the swing blade, and is mainly used for taking blood from infants' heels and other body parts as well.

BACKGROUND OF THE INVENTION

The lancet is widely used in various medical units as a medical instrument for taking blood from the human body. The existing lancets can be divided into a puncture lancet and an incision lancet according to the different blood-taking methods. The puncture lancet acts on the blood-taking site by means of acupuncture, mainly used for taking blood from an adult's finger. The incision lancet acts on the blood-taking site by means of blade incision. The incision lancet feels less painful than the acupuncture lancet, and can take enough amount of blood, and therefore it is especially suitable for infants, particularly for taking blood from newborns' heels.

American patent U.S. Pat. No. 5,314,441 discloses a disposable cutting lancet assembly, i.e. an incision lancet. Such a lancet uses a blade, and realizes the blood-taking purpose by incising the blood-taking site with an incising action. The incising action is mainly performed by a supporting arm of the blade that moves along a copying track slot under the push of a spring. The supporting arm of the blade is provided with a pivot pin, which is located in the copying track slot. When the movement starts, the blade is stretched out of the casing, and performs the incising movement, and is then retracted into the casing again via a path of "water drop" form. Such an incision blood-taking mechanism is simple in structure and reliable in movement, especially suitable for taking blood from infants' heel. However, because of the combination of the supporting arm of the single blade and the copying track slot, the movement track of the point of the blade is of an arc, which is more difficult in controlling incision depth and incision width; in other words, because of limitation of the mechanism, it is very difficult to accurately obtain the incision depth within the range of 0.5~2 mm and the incision width within the range of 2.5~3 mm. Therefor, a problem that the present invention emphasizingly studies is how to design a new incision blood-taking mechanism, so as to meet the requirement on controlling the incision depth and the incision width.

CONTENTS OF THE INVENTION

Aiming at meeting the requirement on controlling the incision depth and the incision width by designing a new incision blood-taking mechanism, the present invention provides A disposable incision safety lancet suitable for taking blood from infants' heels, so as to resolve the existing technical problem on this aspect.

In order to attain the above-mentioned purpose, a technical solution of the present invention is as below: A disposable incision safety lancet is provided, which includes a casing and a trigger. It is innovative on the following aspects: The casing is provided inside with an incision blood-taking mechanism composed of a cam, a main swing arm, a secondary swing arm, a blade and a spring, where:

the cam is rotatably fixed in the casing via a pivot; the spring, as a driving element of the incision blood-taking mechanism, is positioned between the cam and the casing, and acts on the rotary direction of the cam; the trigger, as a triggering control member of the incision blood-taking mechanism, is positioned on the casing; in a pre-triggering state, an action portion of the trigger is propped against a lock gate provided on the cam, and forces the spring to be in an energy storage state, with a triggering portion of the trigger being stretched out of the casing;

the main swing arm, as the first swing arm, is provided with a locating end and a swing end, the locating end being positioned in the casing, the swing end being hung in the casing; this swing end is provided with a working face, which is contactively matched with flange of the cam; the flange of the cam is provided, corresponding to this working face, with a curved surface, whose curvature radius is transient from a first radius (R1) to a second radius (R2); this curved surface forces the main swing arm to make a first swing with rotation of the cam, with the distance from center of the locating end itself to the point of the blade as a third radius (R3);

the secondary swing arm, as the second swing arm, is provided with a locating end and a swing end; the locating end of the secondary swing arm is connected with the swing end of the main swing arm fittedly and rotatably via a pin and a hole, and an initial rotation-angle orientation is realized by means of a contactively propped structure provided mutually and correspondingly in the rotation direction; the blade is fixedly mounted on the swing end of the secondary swing arm; the secondary swing arm is provided in the rotary direction with a toggle face, corresponding to which is a toggle pin provided on the cam; this toggle pin acts on the toggle face on the secondary swing arm with rotation of the cam, and forces the secondary swing arm to make a second swing with the distance from center of the locating end itself to the point of the blade as a fourth radius (R4);

the blade is located at a blood-taking opening provided on the casing; when the incision blood-taking mechanism makes the first swing, the point of the blade is swingingly stretched out of the casing from the blood-taking opening along a first arc-shaped path (A); when the incision blood-taking mechanism makes the second swing, the point of the blade is swingingly retracted into the casing along a second arc-shaped path (B).

The explanation for the relevant contents of the above technical solution is as below:

1. In the above solution, the "spring" is the driving element of the incision blood-taking mechanism, and can specifically be selected from the group consisting of a tension spring, a compression spring, a torsion spring and a flat spring. Various kinds of spring can be selected to drive the cam to rotate after the connection relation among each part of the incision blood-taking mechanism has been determined.

2. In the above solution, the "contactively-propped structure" is the initial rotation-angle orientation structure of the secondary swing arm relative to the main swing arm. The second swing arm (the secondary swing arm) can only rotate relative to the first swing (the main swing arm) after the locating end of the second swing arm is connected with the swing end of the first swing arm via the pin and the hole fittedly and rotatably. Because the blade is provided at the swing end of the second swing arm, there is an initial rotation-angle orientation problem with the second swing arm relative to the first swing arm. Such locating is realized by the "contactively-propped structure". The contactively-propped structure includes the following two kinds of varieties and the improvement solution thereof:

(1) The contactively-propped structure is composed of a hook body and a hook mouth fitted together, one of which is provided on the main swing arm and the other on the secondary swing arm, both contactively propped to form the initial rotation-angle orientation of the secondary swing arm relative to the main swing arm; and (2) the contactively-propped structure is composed of a propping block and a propping face, one of which is provided on the main swing arm and the other on the secondary swing arm, both contactively propped to form the initial rotation-angle orientation of the secondary swing arm relative to the main swing arm.

3. In the above solution, the "trigger" is the triggering control member of the incision blood-taking mechanism, and the incision blood-taking mechanism is driven to perform the incision blood-taking action by means of triggering the control member. The following two kinds of structures are adopted for the trigger (however, other structures can also be adopted):

(1) A pushingly-triggered structure, composed of a pushingly-triggered key slidely located on the casing; the front end of the pushingly-triggered key is the action portion, and the rear end the triggering portion, with a protection sleeve being clipped as a safety structure between the triggering portion and the casing; and (2) a push structure, composed of a push lever rotatably located on the casing; the front end of the push lever is the action portion, and the rear end the triggering portion, with a protection seat being clipped as a safety structure between the triggering portion and the casing.

The designing concept of the present invention is as below: The first swing arm is pushed to make the first swing with the third radius R3 as the radius by means of the curved surface of the flange of the cam mechanism, making the point of the blade realize the first swing with the first arc-shaped path A as the track; then the toggle face on the second swing arm is acted on by means of the toggle pin provided on the cam mechanism, driving the second swing arm to make the second swing with the fourth radius R4 as the radius; the point of the blade is made to continue to realize the second swing with the second arc-shaped path B as the track. The first swing makes the point of the blade stretch out of the casing from the blood-taking opening, and the second swing makes the point of the blade be retracted into the casing. Connection of the two swings makes the point of the blade incise a V-formed path composed of two arcs of different shape connected with each other, producing an incision action characterized by the V-formed path; the distance from the connection point of the first arc-shaped path A and the second arc-shaped path B to the blood-taking opening of the casing is the incision depth H, and the width of the first arc-shaped path A and the second arc-shaped path B exceeding the blood-taking opening is the incision width W. The incision depth H is dependent on the difference between the second radius R2 and the first radius R1 of the curved surface of the flange of the cam, i.e. R2−R1=incision depth H+reserved distance for the point of the blade in the casing; the incision width W is controlled by the swing radius of the first swing arm (the third radius R3) and the swing radius of the second swing arm (the fourth radius R4). An incision of different blood-taking depth and blood-taking width can be designed by changing the dimension of R1~R4.

Because of application of the above technical solution, the present invention has the following advantages and effects compared with the prior art:

1. The present invention combines the two arc-shaped tracks obtained from the two swing mechanisms, the first swing arm and the second swing arm, via the cam and the toggle pin provided on the cam effectively and interlockingly, thus making the point of the blade incise the V-formed path composed of two arcs of different shape connected with each other. Such a double-swing-arm design is not only novel in structure, clever in concept and reliable in working, but also has outstanding substantial characteristics and technical improvement compared with the prior art.

2. For the incision blood-taking mechanism of the lancet of the present invention, an incision of different blood-taking depth and different blood-taking width can be designed by means of changing the dimension of R1~R4, which better meets the requirement on controlling incision depth and incision width, resolving the existing technical problems on this aspect.

3. The incision blood-taking mechanism of the present invention adopts the design of the double-swing-arm combination structure; compared with the prior art single-swing-arm structure, the mechanism moves with higher accuracy and controllability, especially suitable for taking blood from infants' heel.

BRIEF DESCRIPTION OF THE DRAWINGS

FIG. 5 is a front view of the cam according to Embodiment 1 of the present invention;

FIG. 6 is a front stereoscopic view of the cam according to Embodiment 1 of the present invention;

FIG. 7 is a back stereoscopic view of the cam according to Embodiment 1 of the present invention;

FIG. 8 is a front view of the main swing arm according to Embodiment 1 of the present invention;

FIG. 9 is a front stereoscopic view of the main swing arm according to Embodiment 1 of the present invention;

FIG. 10 is a front view of the secondary swing arm and the blade according to Embodiment 1 of the present invention;

FIG. 11 is a front stereoscopic view of the secondary swing arm and the blade according to Embodiment 1 of the present invention;

FIG. 12 is a back stereoscopic view of the secondary swing arm and the blade according to Embodiment 1 of the present invention;

FIG. 13 is a rear view of the secondary swing arm and the blade according to Embodiment 1 of the present invention;

Figure 1:
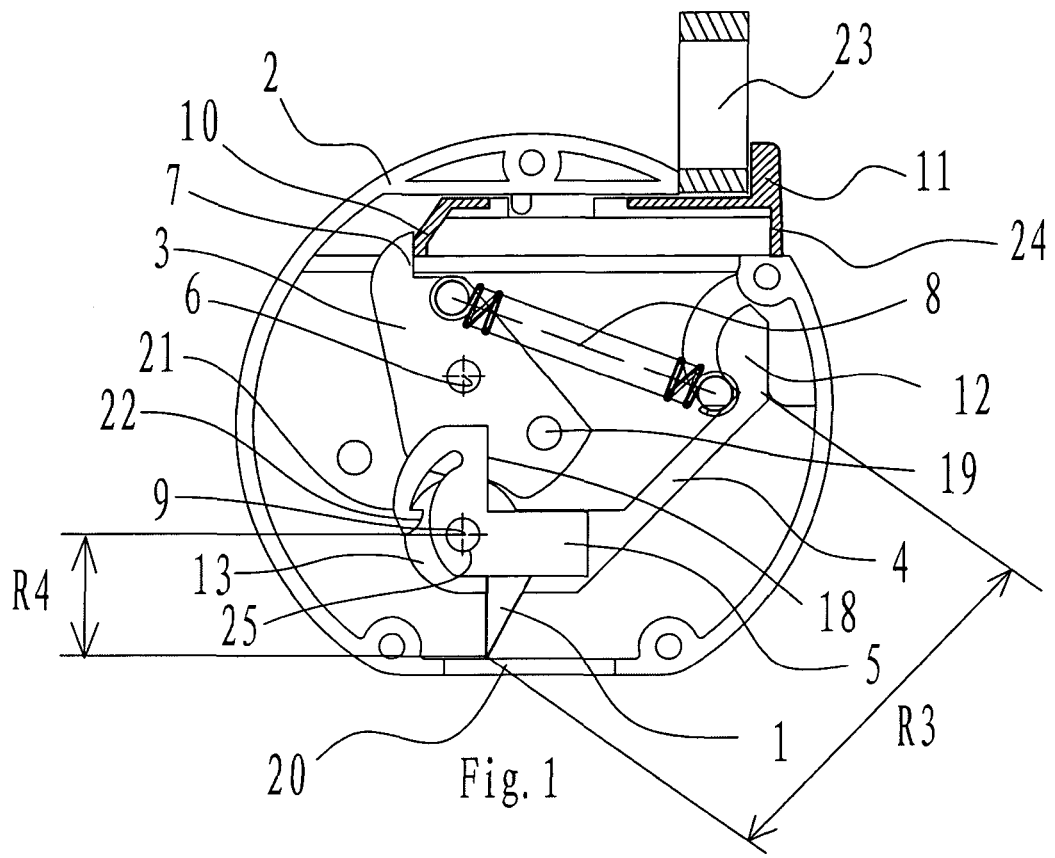
FIG. 1 is a schematic view of the pre-projection state according to Embodiment 1 of the present invention.

In the figures above: 1. Blade; 2. casing; 3. cam; 4. main swing arm; 5. secondary swing arm; 6. pivot; 7. lock gate; 8. spring; 9. pin axis; 10. action portion; 11. triggering portion; 12. locating end; 13. swing end; 14. working face; 15. curved surface; 16. locating end; 17. swing end; 18. toggle face; 19. toggle pin; 20. blood-taking opening; 21. hook body; 22. hook mouth; 23. protection sleeve; 24. pushingly-triggered key; 25. hole; 26. torsion spring; R1. the first radius; R2. the second radius; R3. the third radius; R4. the fourth radius; A. the first arc-shaped path; B. the second arc-shaped path; C. propping face; H. incision depth; and W. incision width.

DETAILED DESCRIPTION OF THE EMBODIMENTS

The present invention will be further described below with reference to drawings and embodiments.

Embodiment 1

A Disposable Incision Safety Lancet

As shown in FIG. 13, this incision lancet includes the casing 2, the trigger, and the blood-taking mechanism provided in the casing 2. The casing 2 is composed of two half casings, an upper cover and a lower cover. The trigger is of a pushingly-triggered structure, which is mainly composed of the pushingly-triggered key 24 slidely located on the casing 2. The front end of the pushingly-triggered key 2 is the action portion 10, and the rear end the triggering portion 11.

The incision blood-taking mechanism is composed of the cam 3, the main swing arm 4, the secondary swing arm 5, the blade 1 and the spring 8. The structure of the cam 3 is shown in FIGS. 5~7, the structure of the main swing arm 4 in FIGS. 8~9, the structure of the secondary swing arm 5 and the blade 1 in FIGS. 10~13.

As shown in FIGS. 1~3 and 5~13, structure of and interconnection among all the parts of the incision blood-taking mechanism are as below:

The cam 3 is rotatably fixed in the casing 2 via the pivot 6. The spring (8) (a tension spring is adopted in FIGS. 1~3), as a driving element of the incision blood-taking mechanism, is positioned between the cam 3 and the casing 2, and acts on the rotary direction of the cam 3. The pushingly-triggered key 2, as a triggering control member of the incision blood-taking mechanism, is slidely positioned on the casing 2. In a pretriggering state, the action portion 10 of the pushingly-triggered key 2 is propped against the lock gate 7 provided on the cam 3, and forces the spring 8 to be in the energy storage state, with the triggering portion 11 of the pushingly-triggered key 2 being stretched out of the casing 2. The protection sleeve 23 is clipped as a safety structure between the triggering portion 11 and the casing 2, so as to prevent the incision blood-taking mechanism from being unintentionally driven.

The main swing arm 4, as the first swing arm, is provided with the locating end 12 and the swing end 13, the locating end 12 being positioned in the casing 2, the swing end 13 being hung in the casing 2. The swing end 13 is provided with the working face 14, which is contactively matched with flange of the cam 3. The flange of the cam 3 is provided, corresponding to this working face 14, with the curved surface 15, whose curvature radius is transient from the first radius R1 to the second radius R2, where the second radius R2 is bigger than the first radius R1. While in working, this curved surface 15 forces the main swing arm 4 to make the first swing with rotation of the cam 3, with the distance from center of the locating end 12 itself to the point of the blade 1 as the third radius R3.

The secondary swing arm 5, as the second swing arm, is provided with the locating end 16 and the swing end 17. The locating end 16 of the secondary swing arm 5 is connected with the swing end 13 of the main swing arm 4 fittedly and rotatably via the pin axis 9 and the hole 25, and the initial rotation-angle orientation is realized by means of a contactively propped structure provided mutually and correspondingly in the rotation direction. The contactively-propped structure is composed of the hook body 21 and the hook mouth 22 fitted together, the hook body 21 being provided on the secondary swing arm 5, the hook mouth 22 being provided on the main swing arm 4, both contactively propped to form the initial rotation-angle orientation of the secondary swing arm 5 relative to the main swing arm 4. The blade 1 is fixedly mounted on the swing end 17 of the secondary swing arm 5. The secondary swing arm 5 is provided in the rotary direction with the toggle face 18, corresponding to which is a toggle pin 19 provided on the cam 3. This toggle pin 19 acts on the toggle face 18 on the secondary swing arm 5 with rotation of the cam 3, and forces the secondary swing arm 5 to make a second swing with the distance from center of the locating end 16 itself to the point of the blade 1 as the fourth radius R4.

Figure 2:
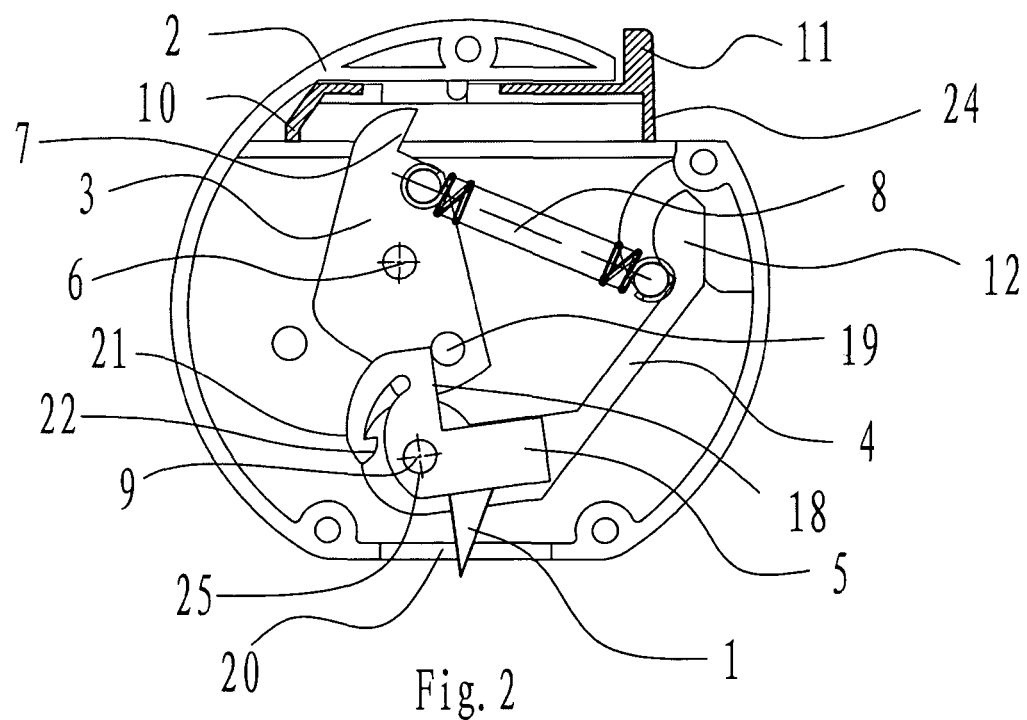
FIG. 2 is a schematic view of the state during projection according to Embodiment 1 of the present invention.
Figure 3:
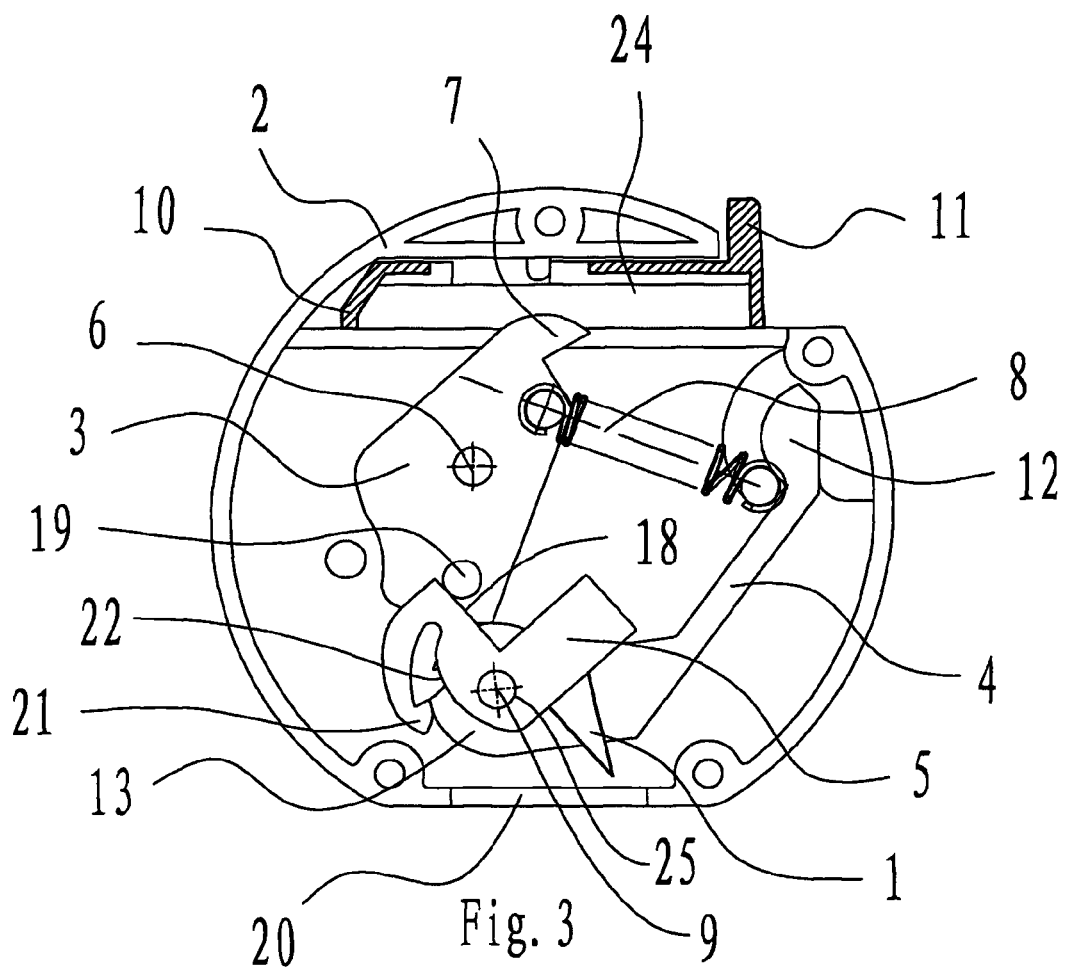
FIG. 3 is a schematic view of the post-projection state according to Embodiment 1 of the present invention.
Figure 4:
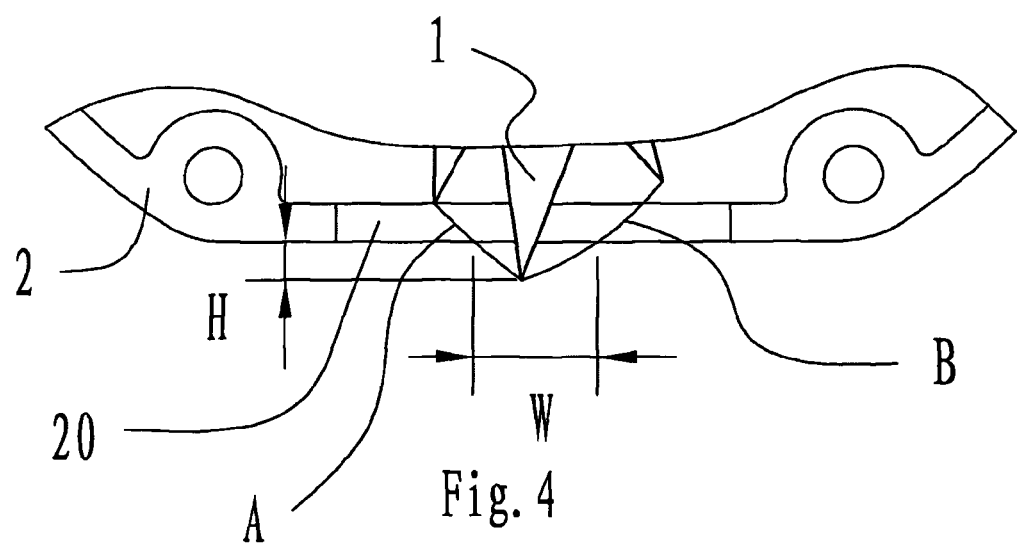
FIG. 4 is a diagram of the movement track of the point of the blade during projection according to Embodiment 1 of the present invention.

As shown in FIG. 4, the blade 1 is located at the blood-taking opening 20 provided on the casing 2. When the lancet is used, first the protection sleeve 23 as shown in FIG. 1 is extracted, then the triggering portion 11 is pushed with a finger, making the action portion 10 of the pushingly-triggered key 2 escape from the lock gate 7 of the cam 3 and be in the state as shown in FIG. 2. Here the spring 8 (a tension spring) pulls the cam 3 to rotate round the center of the pivot 6; and the curved surface 15 of the cam 3, with rotation of the cam 3, forces the main swing arm 4 to make the first swing with the third radius R3 as the radius. Since here the secondary swing arm 5 swings with the main swing arm 4, the point of the blade 1 is swingingly stretched out of the casing 2 from the blood-taking opening 20 along the first arc-shaped path A. When the cam 3 continues to rotate, the toggle pin 19 on the cam 3 pushes the toggle surface 18 on the secondary swing arm 5, and forces the secondary swing arm 5 to make the second swing with the fourth radius R4 as the radius. The point of the blade 1 is swingingly retracted into the casing 2 along the second arc-shaped path B, thus obtaining a V-formed path composed of two arcs of different shape connected to each other.

In this embodiment, the contactively-propped structure can also be replaced by other structures. For example, this contactively-propped structure is composed of a propping block (not shown in the figures) and a propping face C (the C portion as shown in FIG. 9) fitted together; the propping block is extensively provided on the secondary swing arm 5, the propping face C is the top face of the swing end of the main swing arm 4 (the C portion as shown in FIG. 9), both contactively propped to form the initial rotation-angle orientation of the secondary swing arm 5 relative to the main swing arm 4. The trigger can also be of a push structure instead; for example, the trigger is composed of a push lever rotatably located on the casing 2, the front end of the push lever being the action portion 10, the central portion being the fulcrum of the rotation, the rear end being the triggering portion 11. A protection seat (not shown in the figures) is clipped as a safety structure between the triggering portion 11 and the casing 2. While in use, first the protection seat is extracted, and then the triggering portion 11 pushed, making the action portion 10 escape from the lock gate 7 of the cam 3 and enter the projection state.

The incision depth H and the incision width W of the blood-taking incision of the embodiment can be designed into such different specifications as 1 mm×2.5 mm, 0.85 mm×1.75 mm, and 0.65 mm×1.4 mm.

Embodiment 2

A Disposable Incision Safety Lancet

Figure 14:
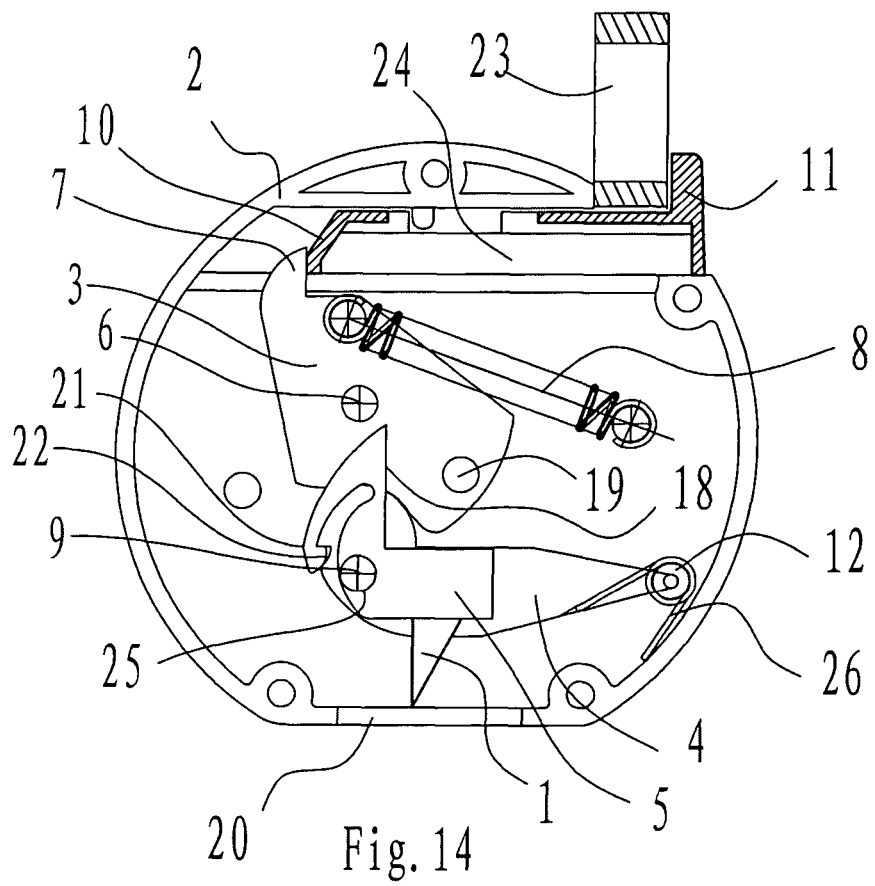
FIG. 14 is a schematic view of the pre-projection state according to Embodiment 2 of the present invention.
Figure 15:
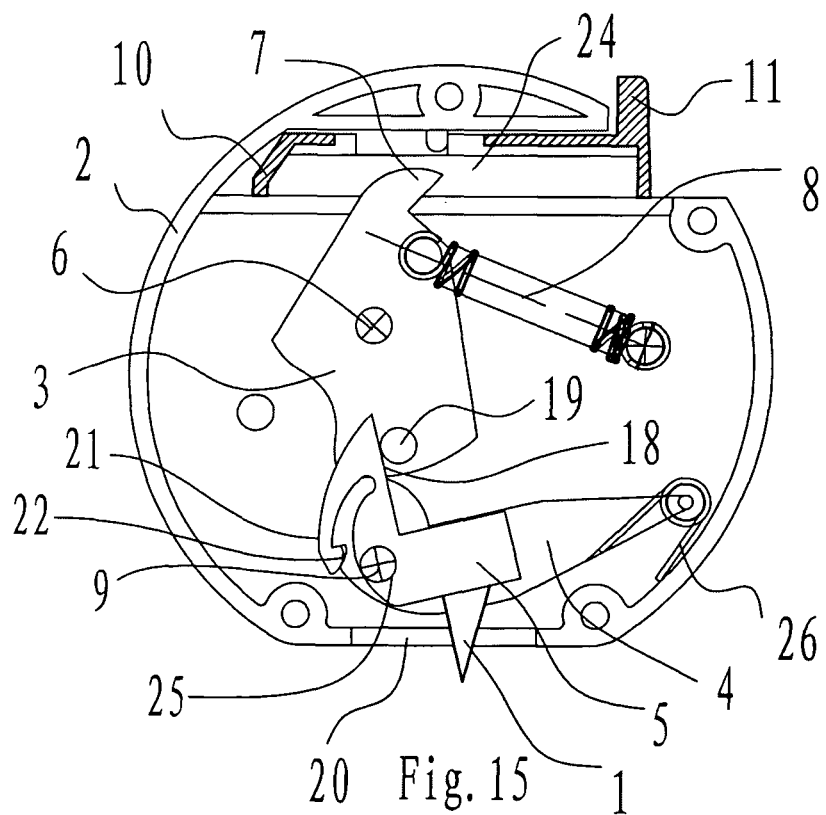
FIG. 15 is a schematic view of the state during projection according to Embodiment 2 of the present invention.
Figure 16:
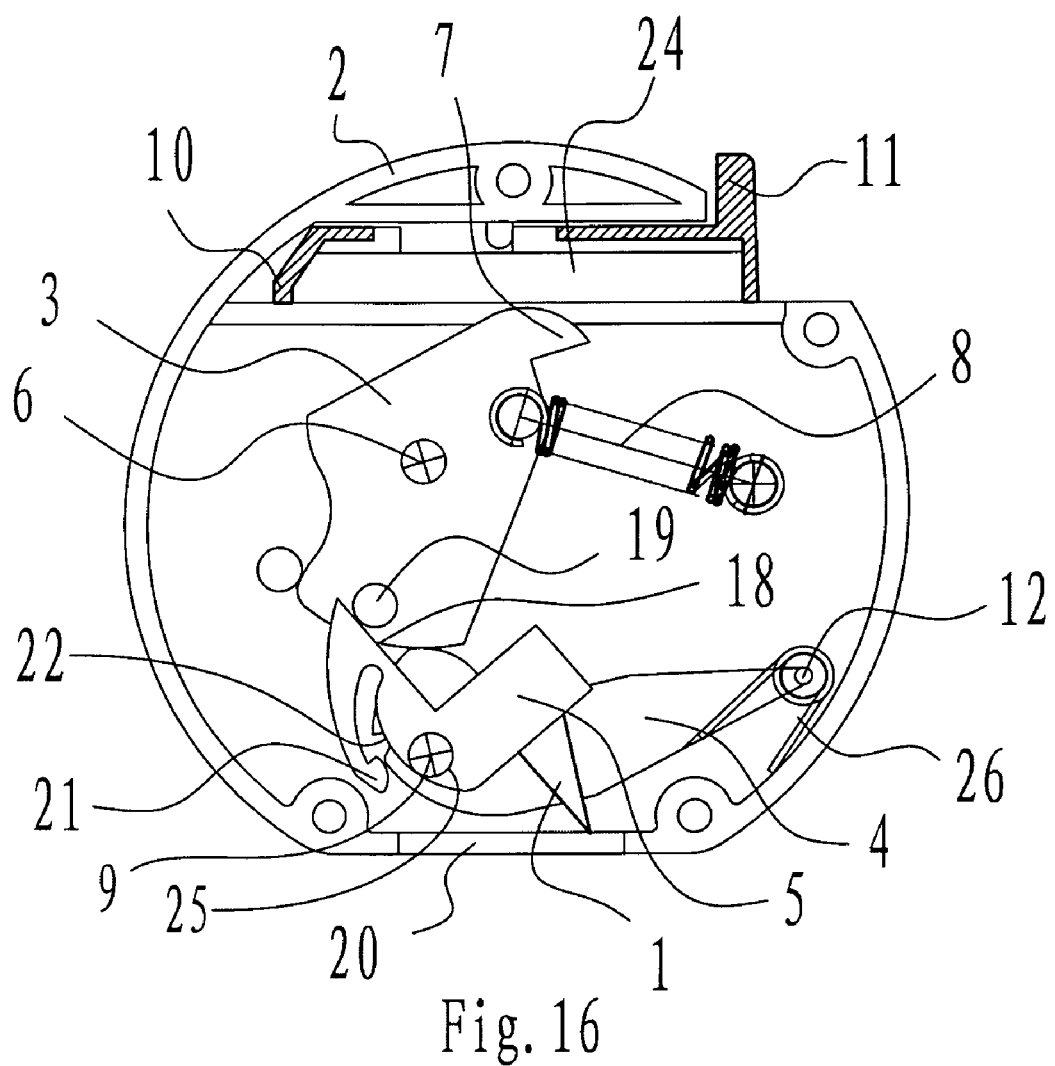
FIG. 16 is a schematic view of the post-projection state according to Embodiment 2 of the present invention.

As shown in FIGS. 14~16, this incision lancet is different from that in Embodiment 1 on the following aspects: First, the locating position of the locating end 12 of the main swing arm 4 in the casing 2 is different from that in Embodiment 1; second, the locating end 12 of the main swing arm 4 is provided with the torsion spring 26, which forces the swing end 13 of the main swing arm 4 stick to the flange of the cam 3; and third, the specific dimensions of R1~R4 are different. The incision depth H and the incision width W of the blood-taking incision of the embodiment can be designed into such different specifications as 2 mm×3 mm.

The above embodiment is used only for explaining the technical concept and characteristics of the present invention. It is provided to make those skilled in the art understand the present invention and implement it, and cannot thereby limit the extent of protection of the present invention. All equivalent changes or modifications according to the spirit of the present invention should fall within the extent of protection of the present invention.

What is claimed is:

1. A disposable incision safety lancet, comprising:
a casing (2) and a trigger;
wherein:
the casing (2) is provided inside with an incision blood-taking mechanism composed of a cam (3), a main swing arm (4), a secondary swing arm (5), a blade (1) and a spring (8);
the cam (3) is rotatably fixed in the casing (2) via a pivot (6); the spring (8), as a driving element of the incision blood-taking mechanism, is positioned between the cam (3) and the casing (2), and acts on the rotary direction of the cam (3); the trigger, as a triggering control member of the incision blood-taking mechanism, is positioned on the casing (2); in a pre-triggering state, an action portion (10) of the trigger is propped against a lock gate (7) provided on the cam (3), and forces the spring (8) to be in an energy storage state, with a triggering portion (11) of the trigger being stretched out of the casing (2);
the main swing arm (4), as the first swing arm, is provided with a locating end (12) and a swing end (13), the locating end (12) being positioned in the casing (2), the swing end (13) being hung in the casing (2); the swing end (13) is provided with a working face (14), which is contactively matched with flange of the cam (3); the flange of the cam (3) is provided, corresponding to this working face (14), with a curved surface (15), whose curvature radius is transient from a first radius (R1) to a second radius (R2); this curved surface (15) forces the main swing arm (4) to make a first swing with rotation of the cam (3), with the distance from center of the locating end (12) itself to the point of the blade (1) as a third radius (R3);
the secondary swing arm (5), as the second swing arm, is provided with a locating end (16) and a swing end (17); the locating end (16) of the secondary swing arm (5) is connected with the swing end (13) of the main swing arm (4) fittedly and rotatably via a pin and a hole, and an initial rotation-angle orientation is realized by means of a contactively-propped structure provided mutually and correspondingly in the rotation direction; the blade (1) is fixedly mounted on the swing end (17) of the secondary swing arm (5); the secondary swing arm (5) is provided in the rotary direction with a toggle face (18), correspondingly to which is a toggle pin (19) provided on the cam (3); this toggle pin (19) acts on the toggle face (18) on the secondary swing arm (5) with rotation of the cam (3), and forces the secondary swing arm (5) to make a second swing with the distance from center of the locating end (16) itself to the point of the blade (1) as a fourth radius (R4);
the blade (1) is located at a blood-taking opening (20) provided on the casing (2); when the incision blood-taking mechanism makes the first swing, the point of the blade (1) is swingingly stretched out of the casing (2) from the blood-taking opening (20) along a first arc-shaped path (A); when the incision blood-taking mechanism makes the second swing, the point of the blade (1) is swingingly retracted into the casing (2) along a second arc-shaped path (B).

2. The incision lancet according to claim 1, wherein the contactively-propped structure is composed of a hook body (21) and a hook mouth (22) fitted together, one of which is provided on the main swing arm (4) and the other on the secondary swing arm (5), both contactively propped to form the initial rotation-angle orientation of the secondary swing arm (5) relative to the main swing arm (4).

3. The incision lancet according to claim 1, wherein the contactively-propped structure is composed of a propping block and a propping face, one of which is provided on the main swing arm (4) and the other on the secondary swing arm (5), both contactively propped to form the initial rotation-angle orientation of the secondary swing arm (5) relative to the main swing arm (4).

4. The incision lancet according to claim 1, wherein the trigger is of a pushingly-triggered structure, and composed of a pushingly-triggered key (24) slidely located on the casing (2); the front end of the pushingly-triggered key (24) is the action portion (10), and the rear end the triggering portion (11), with a protection sleeve (23) being clipped as a safety structure between the triggering portion (11) and the casing (2).

5. The incision lancet according to claim 1, wherein the trigger is of a push structure, and composed of a push lever rotatably located on the casing (2); the front end of the push lever is the action portion (10), and the rear end the triggering portion (11), with a protection seat being clipped as a safety structure between the triggering portion (11) and the casing (2).

* * * * *